(12) United States Patent
McCloskey et al.

(10) Patent No.: US 11,109,973 B2
(45) Date of Patent: Sep. 7, 2021

(54) SYSTEM FOR EVALUATION OF PROSTHETIC HEART VALVES UNDER STEADY HYDRODYNAMIC CONDITIONS

(71) Applicant: BIOMEDICAL DEVICE CONSULTANTS AND LABORATORIES OF COLORADO, LCC, Wheat Ridge, CO (US)

(72) Inventors: Benjamin McCloskey, Lakewood, CO (US); Craig Weinberg, Golden, CO (US)

(73) Assignee: Biomedical Device Consultants and Laboratories of Colorado, LLC, Wheat Ridge, CO (US)

( * ) Notice: Subject to any disclaimer, the term of this patent is extended or adjusted under 35 U.S.C. 154(b) by 0 days.

(21) Appl. No.: 17/151,104

(22) Filed: Jan. 15, 2021

(65) Prior Publication Data
US 2021/0212830 A1    Jul. 15, 2021

Related U.S. Application Data

(60) Provisional application No. 62/961,354, filed on Jan. 15, 2020.

(51) Int. Cl.
*G09B 23/30* (2006.01)
*A61F 2/24* (2006.01)
*A61M 60/871* (2021.01)

(52) U.S. Cl.
CPC ......... *A61F 2/2472* (2013.01); *A61M 60/871* (2021.01)

(58) Field of Classification Search
CPC ...... G09B 23/28; G09B 23/30; G09B 23/303; A61F 2/2472
See application file for complete search history.

(56) References Cited

U.S. PATENT DOCUMENTS

| 4,682,491 A | 7/1987 | Pickard |
| 5,176,153 A | 1/1993 | Eberhardt |

(Continued)

FOREIGN PATENT DOCUMENTS

| CN | 201076529 Y | 6/2008 |
| CN | 102415919 A | 4/2012 |

(Continued)

OTHER PUBLICATIONS

Fisher, "Design of a function test apparatus for prosthetic heart valves," Clinical Physics and Physiological Measurement, (1986), 7(1):63-73, Abstract Only.

(Continued)

*Primary Examiner* — Kurt Fernstrom
(74) *Attorney, Agent, or Firm* — Dorsey & Whitney LLP (57) ABSTRACT

Steady flow hydrodynamic performance testing is performed on a valved prosthesis mounted in a test conduit. The system is configured with prescribed test condition inputs into control software. Upon test initiation, a steady flow pump is activated and automatically adjusts its flow based on the software logic to meet the prescribed first test condition. During forward flow pressure drop testing, the flow pump is automatically adjusted to achieve and hold a particular flow rate. During back flow leakage testing, the steady flow pump is automatically adjusted to achieve and hold a particular differential pressure across the test prosthesis while a flow rate of the leakage flow is measured. After a first test condition has been achieved, the system control software then automatically adjusts the pump flow rate to meet a second test condition. This process then continues until all conditions set by software inputs are evaluated.

26 Claims, 7 Drawing Sheets

(56) References Cited

U.S. PATENT DOCUMENTS

| | | | |
|---|---|---|---|
| 5,272,909 A * | 12/1993 | Nguyen | A61F 2/2472 600/481 |
| 5,406,857 A | 4/1995 | Eberhardt et al. | |
| 5,584,878 A | 12/1996 | Love et al. | |
| 5,899,937 A * | 5/1999 | Goldstein | C12M 21/08 623/2.11 |
| 6,062,075 A * | 5/2000 | Ritz | A61F 2/2472 607/119 |
| 6,730,122 B1 | 5/2004 | Pan et al. | |
| 7,326,564 B2 | 2/2008 | Lundell et al. | |
| 7,621,192 B2 | 11/2009 | Conti et al. | |
| 8,230,717 B2 | 7/2012 | Matonick | |
| 8,318,414 B2 | 11/2012 | Dancu et al. | |
| 9,417,110 B2 | 8/2016 | Raz et al. | |
| 9,649,217 B2 | 5/2017 | Daniel | |
| 9,662,211 B2 * | 5/2017 | Hodson | G01M 99/00 |
| 9,795,484 B2 | 10/2017 | Daniel | |
| 10,368,984 B2 | 8/2019 | Armstrong | |
| 10,898,329 B2 * | 1/2021 | Marquez | F16K 37/0091 |
| 2003/0066338 A1 | 4/2003 | Michalsky et al. | |
| 2014/0099617 A1 * | 4/2014 | Tallman, Jr. | G09B 23/288 434/262 |
| 2018/0108275 A1 * | 4/2018 | Newberry | A61B 5/02 |
| 2018/0128660 A1 | 5/2018 | Lee | |
| 2019/0272776 A1 * | 9/2019 | Fiore | G09B 23/30 |
| 2020/0046500 A1 | 2/2020 | Lee | |
| 2020/0135057 A1 * | 4/2020 | Fatimi | G09B 23/32 |
| 2020/0359935 A1 * | 11/2020 | Clemensen | A61B 5/087 |

FOREIGN PATENT DOCUMENTS

| | | |
|---|---|---|
| CN | 203519279 U | 4/2014 |
| CN | 104819835 A | 8/2015 |
| CN | 107773328 A | 3/2018 |
| CN | 108175883 A | 6/2018 |
| CN | 109253859 A | 1/2019 |
| CN | 209332382 U | 9/2019 |
| CN | 209332384 U | 9/2019 |
| CN | 110487638 A | 11/2019 |
| CN | 210014975 U | 2/2020 |
| JP | 2005192687 A | 7/2005 |
| JP | 4897477 B2 | 3/2012 |
| JP | 2019136660 A | 8/2019 |
| RU | 2336053 C1 | 10/2008 |

OTHER PUBLICATIONS

Haggag, "A Method for Determination of Pressure Drop in Caged-Ball and Caged-Disc Prosthetic Cardiac Valves," J. King Saud Univ., vol. 1, Eng. Sci. (1,2), pp. 199-212, Riyadh.

Vivitro Labs, "Heart Valve Testing—Steady Flow," https://protomedlabs.equipment/non-classe/heart-valve-testing-steady-flow, obtained May 21, 2020, 3 pages.

Van Nooten, "Artificial heart valves: state of the art," Verh K. Acad. Geneeskd Belg., (2003), 65(3):135-80, Abstract Only.

Walker, "In Vitro Evaluation of Mechanical Heart Valve Performance Using a Novel Test Chamber in an Automated Mock Circulatory Loop," Dissertation, (2010), Virginia Commonwealth University, 137 pages.

Zou et al., "The Development of Control System in Artificial Heart Valves Test Equipment," Proc. World Congress on Intelligent Control and Automation (WCICA), (2006), 2:9411-9415, Abstract Only.

* cited by examiner

SYSTEM FOR EVALUATION OF PROSTHETIC HEART VALVES UNDER STEADY HYDRODYNAMIC CONDITIONS

CROSS REFERENCE TO RELATED APPLICATIONS

This application claims the benefit of priority pursuant to 35 U.S.C. § 119(e) of U.S. provisional application No. 62/961,354 filed 15 Jan. 2020 entitled "System for evaluation of prosthetic heart valves under steady hydrodynamic conditions," which is hereby incorporated herein by reference in its entirety.

TECHNICAL FIELD

The technology described herein relates to systems and methods for hydrodynamic testing of prosthetic valved devices, in particular, but not limited to, prosthetic heart valves and valved conduits under a steady fluid flow environment.

BACKGROUND

Within the cardiovascular system are valves that direct blood flow throughout the body during the cardiac cycle. The valves of the heart, which include the aortic and mitral valves on the left side and the tricuspid and pulmonary valves on the right side, are the most commonly known. Other valves are present in the venous system, specifically in the leg region, to aid in transporting blood back to the heart from the lower extremities. When native valves present with disease or other functional insufficiencies that result in inadequate performance, a prosthetic valve can be implanted to restore blood flow to its desired state.

Functional evaluation of prosthetic valves encompasses many aspects as part of the regulatory approval process, including hydrodynamic performance and lifecycle durability assessment. Within the regime of hydrodynamic performance, the prosthetic valves are subjected to two flow-based test environments, pulsatile and steady flow. Pulsatile flow evaluation aims to accurately mimic the cardiovascular dynamics with pulsatile pressure and flow waveforms. In contrast, steady flow testing characterizes the prosthetic valve's hydrodynamic performance at discrete steady-state flow conditions, either forward through the opened valve for measurement of pressure drop or backward through the closed valve for measurement of leakage.

Steady flow testing historically utilizes two individual test apparatus', one for the forward flow pressure drop assessment and one for the steady back flow leakage assessment. Moreover, the control of the test conditions (i.e., forward flow rate and back pressure) with these systems has typically been managed manually by the operator throughout the test. The result of these combined aspects is that current testing for steady flow hydrodynamic performance can be cumbersome and burdensome in both time and effort during a prosthetic valve development program.

The information included in this Background section of the specification, including any references cited herein and any description or discussion thereof, is included for technical reference purposes only and is not to be regarded subject matter by which the scope of the invention as defined in the claims is to be bound.

SUMMARY

Steady flow hydrodynamic performance testing is accomplished by first securing or deploying the test prosthesis into an appropriately sized rigid or flexible annulus holder, or other appropriate structure that secures the prosthesis. The holder with prosthesis is then secured within the steady flow test apparatus for evaluation. Test system valves are then adjusted either manually by the operator (in one embodiment) or automatically by control software (in another embodiment) to either facilitate flow through the valve in the forward direction, such that the valve will be tested in an opened state, or to facilitate flow in the backward direction, such that the valve will be tested in the closed state.

Once the system is configured for the appropriate test, the operator inputs the prescribed test condition(s) into the system control software and initiates a test. The steady flow pump is then activated and automatically adjusts its flow based on the system's software logic to meet the prescribed first test condition. During forward flow pressure drop testing, the flow pump is automatically adjusted to achieve and hold a particular flow rate. During back flow leakage testing, the steady flow pump is automatically adjusted to achieve and hold a particular differential pressure across the test prosthesis while a flow rate of the leakage flow is measured. After a first test condition has been achieved, the system control software then automatically adjusts the pump flow rate to meet a second test condition. This process then continues until all conditions, as defined by the operator through software inputs, have been evaluated.

In an embodiment where the test system is constructed with electromechanical system valves under computer or processor control, the software logic of the test system may have the ability to automatically adjust the test system valves to direct fluid flow through the test system for evaluation of either forward flow pressure drop or back flow leakage without operator interaction.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

The disclosure will be readily understood by the following detailed description in conjunction with the accompanying drawings, wherein like reference numerals designate like structural elements.

The use of cross-hatching or shading in the accompanying figures is generally provided to clarify the boundaries between adjacent elements, e.g., when shown in cross section, and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Figure 1:
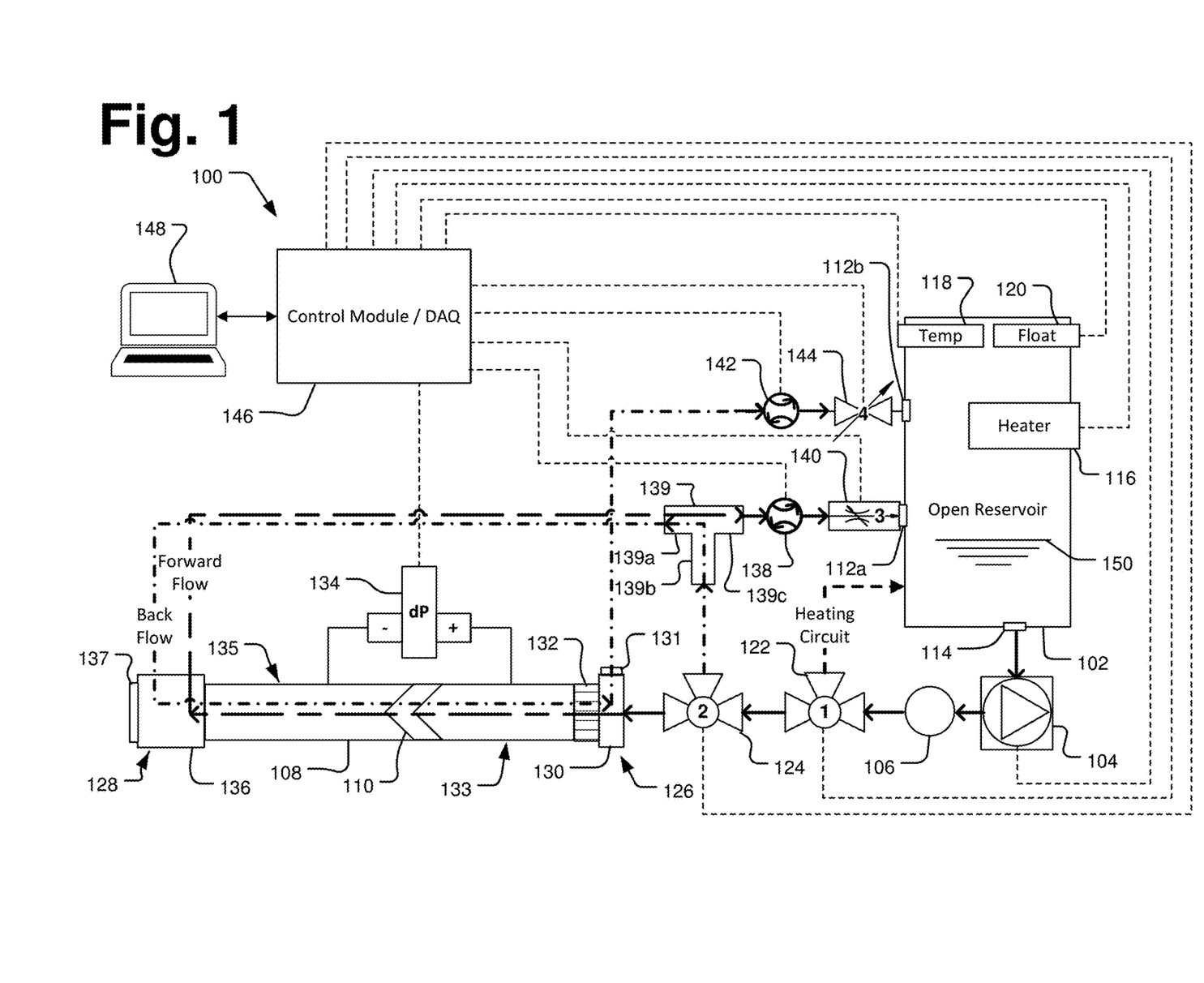
FIG. 1 is a block diagram illustrating steady flow hydrodynamic performance test system for a valve prosthesis including a control system according to embodiments disclosed herein.

An implementation of a test system 100 for steady flow hydrodynamic performance measurement and testing is depicted schematically in FIG. 1. The test system 100 may include a single fluid reservoir 102 in fluid communication with a steady flow pump 104, a compliance chamber 106, a test conduit 108 that houses a test prosthesis holder 110 (and a test prosthesis when in operation), and a series of control valves that direct fluid throughout the test system 100.

The valves and steady flow pump 104 may be under electronic control via a control module 146 that is directed by a software system operating on a connected computer 148. The control module 146 may be directed by the software control program implemented on the computer 148 to open and close valves and change the speed of the steady flow pump 104 in order to create appropriate system conditions for testing a prosthesis. The control module 146 may further include an integrated data acquisition (DAQ) device, which acts as an interface between the computer 148 and various sensors placed within the test system 100. The DAQ conditions incoming signals from sensors and performs an analog to digital signal conversion before transmitting the sensor data to the computer 148 through an integrated bus to be used by the control software on the computer 148 to appropriately adjust components of the test system 100.

A working fluid 150, which may be water, saline, a saline/glycerin solution, a glycerin/water solution or a blood analog or substitute, is employed within the test system and stored within the reservoir 102. The working fluid 150 may be selected to simulate one or more attributes of human blood, such as density or viscosity. For example, in certain instances, physiological saline which does not simulate the viscosity of blood, but simulates density, may be used. In other cases saline/glycerin solution may be employed to simulate both blood density and viscosity.

The system fluid reservoir 102 includes multiple inlet ports 112a/b to receive fluid, one outlet port 114 to supply fluid to the system, a heating element 116, a temperature probe 118, and a level float 120. The fluid reservoir 102 provides a working fluid 150 draw source for the steady flow pump 104. The heating element 116 combined with the temperature probe 118 allows the control module 146 to maintain the working fluid at a specified temperature as defined in the input to the software control program on the computer 148 or preprogrammed into a temperature controller within the control module. Temperature measurements of the working fluid may be returned to the software control program on the computer 148 as part of the data collected during a test cycle. The inlet to the computer-controlled steady flow pump 104 is in fluid connection with the outlet 114 from the fluid reservoir 102 and the outlet of the steady flow pump 104 is in fluid connection with a compliance chamber 106. The computer-controlled steady flow pump 104 is the primary fluid driver for the test system 100 and the compliance chamber 106, located directly at the exit from the steady flow pump 104, functions to dampen and eliminate oscillations that may be produced by the steady flow pump 104 during normal operation.

Two 3-way directional control valves may be positioned in series in fluid connection with the outlet of the compliance chamber 106. The first 3-way control valve 122 aids in system heating by providing an abbreviated circulation path from the reservoir 102, through the steady flow pump 104 and compliance chamber 106, and then directly back to the reservoir 102. When the test system 100 is actuated for prosthesis testing, the first 3-way control valve 122 directs fluid to the second 3-way control valve 124 that is located in fluid connection with the output of the first 3-way control valve 122. The second 3-way control valve 124 may be actuated to direct flow of the working fluid 140 into either a first end 126 of the test conduit 108 for forward flow pressure drop testing of a valve prosthesis or a second end 128 of the test conduit 108 for back flow leakage testing of a valve prosthesis.

In a manually controlled embodiment of the test system 100, the 3-way control valves 122, 124 may be manipulated by an operator and positioned based on a desired system configuration. In an automatically controlled embodiment of the test system 100, the 3-way control valves may be electromechanically operated (e.g., by solenoids) and activated by control software logic of the test system 100 and positioned based on a desired test configuration.

A proximal manifold 130 may be connected to the first end 126 of the test conduit 108 and placed in fluid connection with the second 3-way control valve 124. The proximal manifold 130 may provide an inlet or outlet connection to or from the test conduit 108 depending upon the direction of fluid flow through the test conduit. The proximal manifold 130 may also provide a port 131 for connecting a return conduit to the reservoir 102 as further described below. A flow straightener 132 may be positioned within the proximal manifold 130 to reduce turbulence in the working fluid entering the test conduit 108. In one example implementation, the flow straightener 132 may be formed as array of numerous smaller diameter tubes oriented in parallel with each other and the direction of fluid flow. The small diameter parallel tubes aid in minimizing turbulent, swirling flow or similar type of non-uniform flow streamlines before the working fluid 150 enters the test conduit 108 in a forward flow test configuration.

The test conduit 108 may consist of two parts, a proximal conduit section 133 and distal conduit section 135, with the prosthesis holder 110 for mounting a test prosthesis positioned within a lumen of the test conduit 108 in between the proximal and distal conduit sections 133, 135. A differential pressure transducer 134 with pressure measurement taps may be located in the region of the test prosthesis holder 110. One of the measurement taps may be located on the proximal conduit section 133 and the other measurement tap may be located on the distal conduit section 135, thereby providing for measurement of the differential pressure across the test prosthesis. In another embodiment, two independent pressure transducers may be used instead of the differential pressure transducer 134, with one located on the proximal conduit section 133 and one on the distal conduit section 135. Independent pressure transducer measurement signals may then be routed to the control module 146 for digitization and then to the control software on the computer 148 for subtraction of the pressures to calculate the pressure difference. The test conduit 108 is in fluid connection with the proximal manifold 130 and the distal manifold.

A distal manifold 136 may be provided on the second end 128 of the test conduit 108 and may provide an inlet or outlet connection to or from the test conduit 108 depending upon the direction of fluid flow through the test conduit 108. An integrated viewing window 137 may be provided within the distal manifold 136 to facilitate direct observation of the test prosthesis. The window 137 may be situated to facilitate viewing of the outflow aspect of the test prosthesis. A first conduit in fluid connection with the distal manifold 136 of the test conduit 108 directs the working fluid 150 to and from (depending upon the test performed and the corresponding direction of flow) a 3-way T-connector 136 via a first arm 139a. A second arm 139b of the T-connector 139 receives fluid from the second 3-way control valve 124 when actuated to direct fluid to the T-connector 139 rather than directly to the proximal manifold 130 of the test conduit 108. A third arm 139c of the T-connector 139 allows fluid pass to a first flow meter 138 that is used to measure the flowrate during forward flow pressure drop testing. The first flow meter 138 is in fluid connection with a variable 2-way control valve 140 that is in fluid connection with the test system reservoir 102 via inlet port 112a.

As noted above, the proximal manifold 130 includes a port 131 that is connected via a second conduit to a second flow meter 142 that is used to measure the flow rate of the back flow leakage through the test prosthesis during assessment. The second flow meter 140 is in fluid connection with a 2-way control valve 144 (which may be a variable valve or a two-position (on/off) valve) that is in fluid connection with the fluid reservoir 102 via inlet port 112b.

In one embodiment all the test system valves can be controlled manually, whereby the operator adjusts the valves to direct flow for either forward flow pressure drop or back flow leakage testing. In another embodiment, all the test system control valves are computer controlled, whereby the test system software adjusts the valves to direct flow for either forward flow or back flow testing based on programmed logic.

In another embodiment, the test system 100 is automated and operates the valves and the steady flow pump 104 through the control module 146 under software control by the computer 148. As shown in FIG. 1, the control module 146 is in electronic communication with each of the valves, the heating element 116, and the steady flow pump 104 and is thereby able to send control signals to each of these system components. The control module 146 may be directly wired to each of the valves and the steady flow pump 104 or may be wirelessly connected to each of the components via a wireless transmission protocol (e.g., Bluetooth or a wireless area network). The computer system software directs the control module 146 to send signals to open and close the valves in different combinations to adjust the system flow direction to facilitate testing for either the forward flow pressure drop or back flow leakage based on the test desired. Moreover, the software control can automatically direct the valves to move between the two respective test conditions (forward flow and back flow) without any operator interaction. When a test is completed, the control software may automatically place the valves into a heating circulation configuration to maintain system working fluid at a desired operating temperature (e.g., while valve prostheses are exchanged).

Further, as shown in FIG. 1, the control module 146 is in electronic communication with a number of sensors within the test system 100, e.g., the temperature probe 118, the level float 120, the first and second flow meters 140, 144, and the differential pressure transducer 134, and is thereby able to receive data signals from each of these system components. The control module 146 may include an integrated data acquisition system (or otherwise be connected to such) that receives and conditions the analog data signals received from the sensors and converts them into digital data signals for processing by the control software on the computer 148. The control software uses the sensor data as a feedback loop to make adjustments to the valves, the heating element 116, and the steady flow pump 104 to ensure that the proper conditions (e.g., working fluid temperature, fluid pressure, and flow rate) are maintained in the test system 100 during a test cycle to meet desired standard test requirements.

Figure 2:
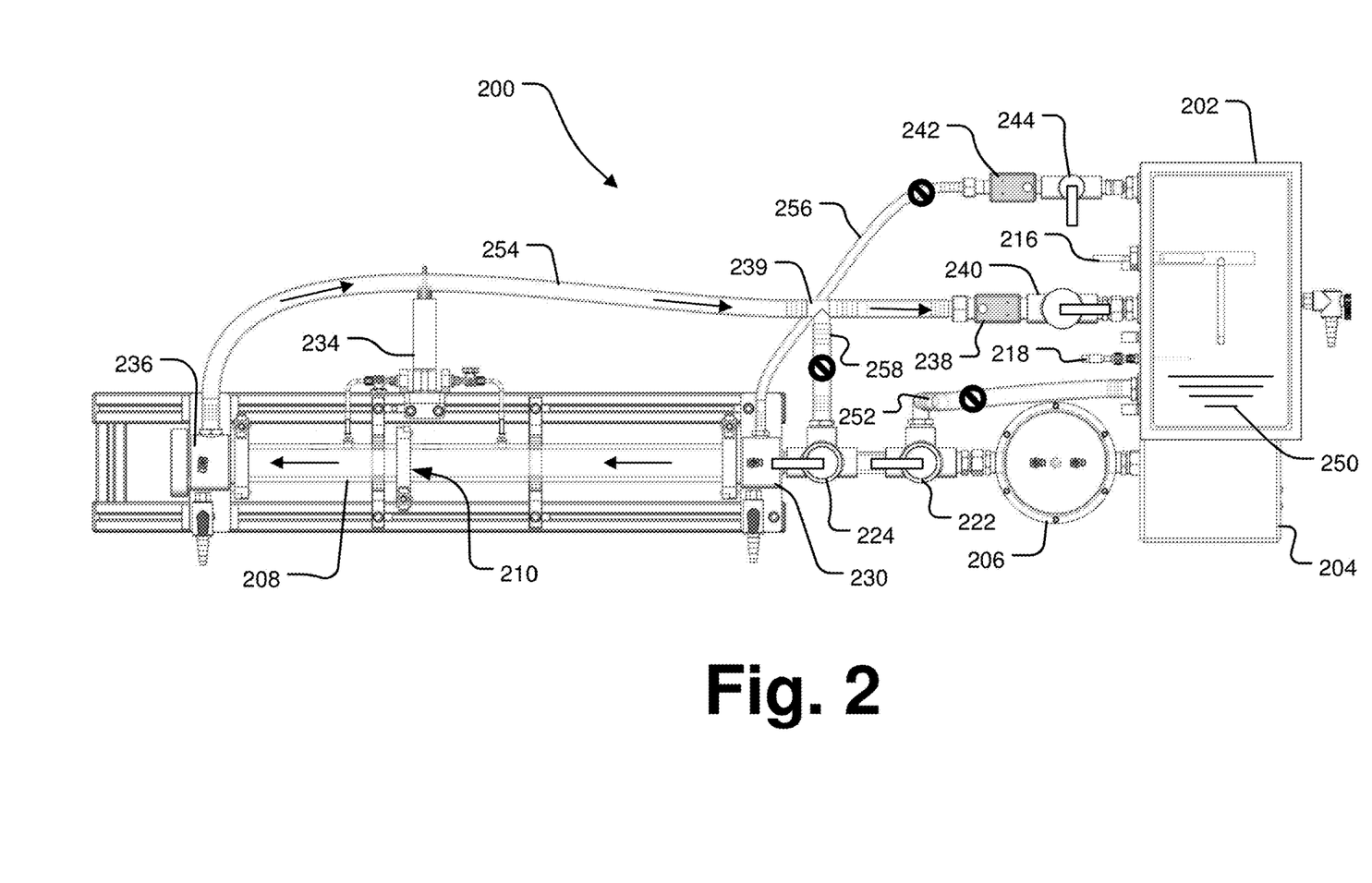
FIG. 2 is a representation of the test system illustrating a forward flow pathway through the test system.

FIG. 2 depicts the test system 200 configured for forward flow testing of a valved prosthesis positioned in the prosthesis holder 210 of the test conduit 208. The arrows in the conduits of the test system 200 of FIG. 2 depict the direction of fluid flow. The valve handles on each of the valves similarly depict the direction of fluid flow through the valves or indicate that the valve is closed. (It should be understood that the valve handles are shown merely as an aid to understanding. As noted above, the valves may be under electromechanical control by the control system and may not be manually operated using manual handles as depicted.) The symbol "⊘" placed over a conduit indicates that there is no fluid flow through the conduit in this configuration. Reference numerals indicating elements not mentioned in the discussion of FIG. 2 correspond to similar reference numerals in FIG. 1 beginning with a "1" rather than a "2" and are provided for ease of orientation of the reader.

In this configuration, working fluid 250 from the reservoir 202 is pumped by the steady flow pump 204 through the compliance chamber 206 and to the first 3-way control valve 222. The first 3-way control valve 222 is open to the second 3-way control valve 224 and thus blocks fluid flow back to the reservoir 202 through the heat circulation conduit 252. The second 3-way control valve 224 is configured to direct fluid in a flow path that enters the test conduit 208 through the proximal manifold 230 such that the working fluid will interact with the valved test prosthesis while it is in an open state. As the valved test prosthesis is open with this configuration, a pressure drop results across the open test valve and the pressure drop is measured by the differential pressure transducer 234 with one measurement port located on the proximal side of the test valve and a second measurement port located on the distal side of the test valve. The fluid flow exits the test conduit 208 through the distal manifold 236 and passes through the first conduit 254 and through the T-connector 239 to the first flow meter 238 for quantification of the fluid flow rate before returning to the fluid reservoir 202 through the variable 2-way control valve 240, which is in a fully open position to maximize flow for metering without any resistance. For forward flow testing, the 2-way valve 244 that is connected to the second flow meter 242 is completely closed, preventing flow through this path through the second conduit 256 or outflow from the reservoir 202. It may be noted that the second conduit 256 may be filled with working fluid 250 from the proximal manifold 230 when the test system 200 begins operation. However, fluid in the second conduit 256 is acts as a dead head due to the closure of the 2-way control valve 244 and does not impact the forward flow of the fluid through the test conduit 208 in the test system 200. Similarly, branch conduit 258 from the T-connector 239 may also be filled with working fluid 250, but this fluid is also a dead head as the position of 3-way control valve 224 prevents fluid flow through it from the direction of the branch conduit 258.

Figure 3:
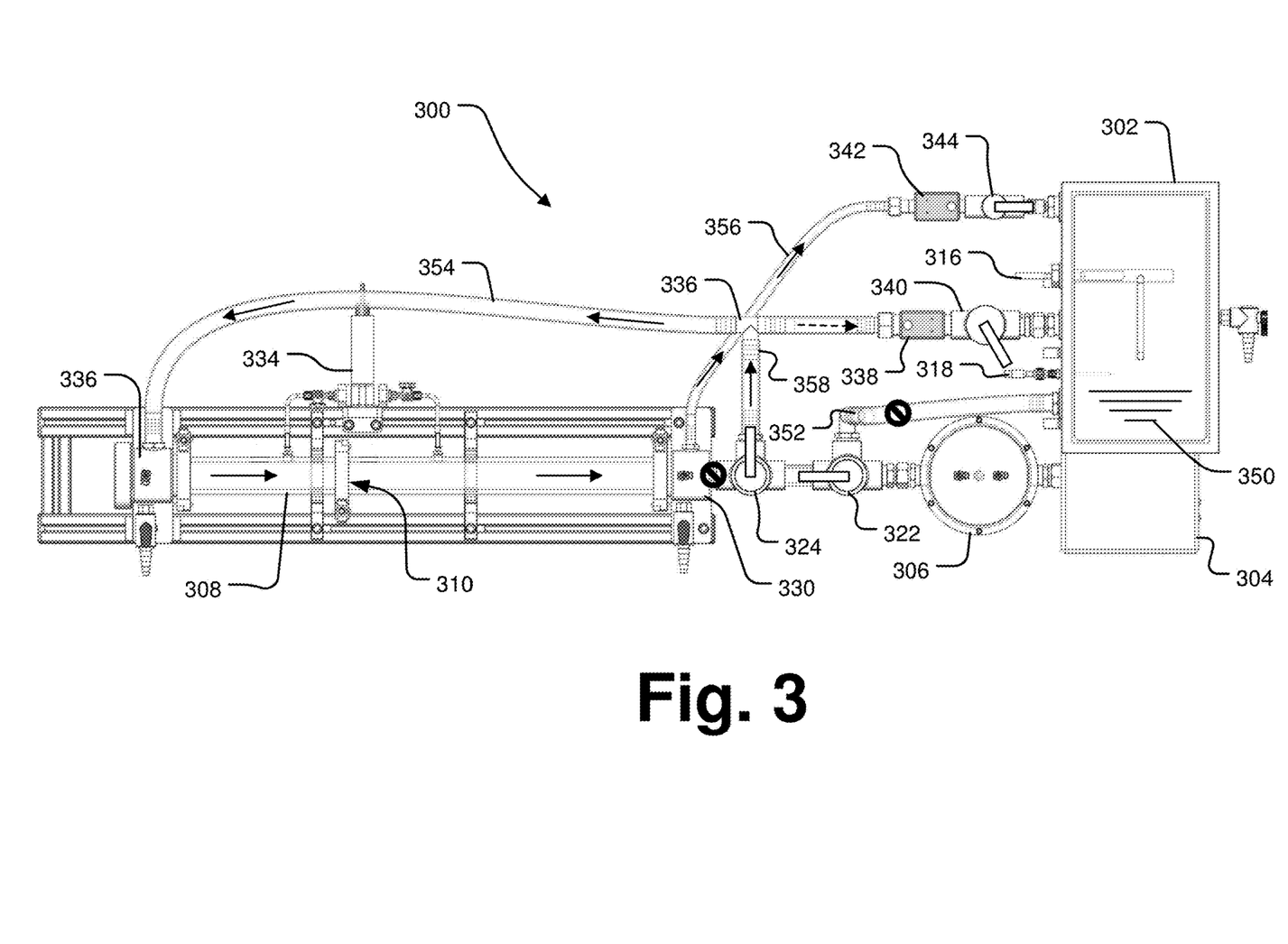
FIG. 3 is a representation of the test system illustrating a back flow leakage flow pathway through the test system.

FIG. 3 depicts the test system 300 configured for back flow leakage testing of a valved prosthesis positioned in the prosthesis holder 310 of the test conduit 308. The arrows in the conduits of the test system 300 of FIG. 3 depict the direction of fluid flow. The valve handles on each of the valves similarly depict the direction of fluid flow through the valves or indicate that the valve is closed. (It should be understood that the valve handles are shown merely as an aid to understanding. As noted above, the valves may be under electromechanical control by the control system and may not be manually operated using manual handles as depicted.) The symbol "⊘" placed over a conduit indicates that there is no fluid flow through the conduit in this configuration. Reference numerals indicating elements not mentioned in the discussion of FIG. 3 correspond to similar reference numerals in FIG. 1 beginning with a "1" rather than a "3" and are provided for ease of orientation of the reader.

In this configuration, working fluid 350 from the reservoir 302 is pumped by the steady flow pump 304 through the compliance chamber 306 and to the first 3-way control valve 322. The first 3-way control valve 322 is open to the second 3-way control valve 324 and thus blocks fluid flow back to the reservoir 302 through the heat circulation conduit 352. The second 3-way control valve 324 is configured to direct fluid in a flow path that enters the branch conduit 258 to the T-connector 239 rather than the flow path to the proximal manifold 330 as in FIG. 2. During back flow leakage or regurgitation testing, the variable 2-way valve 340 in fluid connection with the first flow meter 338 and the reservoir 302 is placed into a mid-position that provides a fluid path for a portion of the working fluid to return to the fluid reservoir 302 during the test process. This reduced return flow through the variable 2-way valve 340 facilitates stability in the test system 300 by allowing the steady flow pump 304 to avoid operating at the lowest end of its capacity, which is not ideal for longevity of the pump motor and leads to poor output flow control.

The balance of the fluid flow is directed through the opposite end of the T-connector 339 through the first conduit 354 to the distal manifold 336 of the test conduit 308. The working fluid 350 thus flows through the test conduit 308 in a reverse direction interacting with the valved test prosthesis mounted in the prosthesis holder 310. Due to the direction of fluid flow, the valved test prosthesis is in a closed position this test configuration. A pressure load is thus created across the closed valve and the differential pressure is measured by the differential pressure transducer 334 with one measurement port located on the proximal side of the test valve and a second measurement port located on the distal side of the test valve. Fluid leakage that passes through the test valve exits the test conduit 308 through the proximal manifold 330 and is directed through the second conduit 356 because the second 3-way control valve 324 outside the proximal manifold 330 is closed to fluid flow from the proximal manifold 330. Working fluid 350 traveling through the second conduit 356 passes through the second flow meter 342 for quantification of the leakage flow before returning to the fluid reservoir 302 through the 2-way control valve 344. The 2-way control valve 344 connected to the second flow meter 342 is completely open in this configuration to maximize flow without any resistance.

Figure 4:
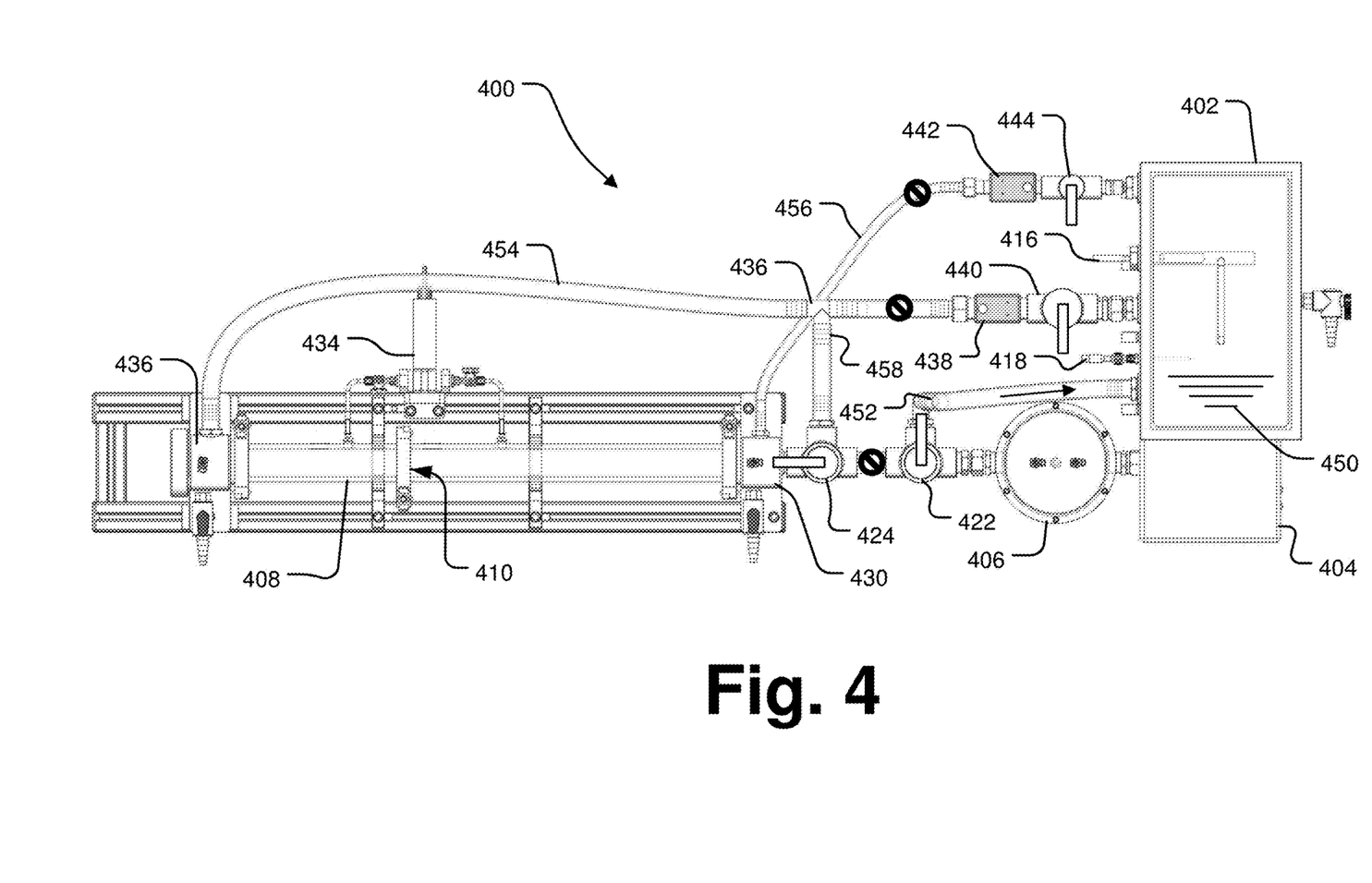
FIG. 4 is a representation of the test system illustrating a heat circulation pathway through the test system.

FIG. 4 depicts the test system 400 configured for providing a circulating heating loop for the working fluid when no test is being conducted, e.g., during a period in which valved prostheses are being exchanged in the prosthesis holder 410 of the test conduit 408. The arrows in the conduits of the test system 400 of FIG. 4 depict the direction of fluid flow. The valve handles on each of the valves similarly depict the direction of fluid flow through the valves or indicate that the valve is closed. (It should be understood that the valve handles are shown merely as an aid to understanding. As noted above, the valves may be under electromechanical control by the control system and may not be manually operated using manual handles as depicted.) The symbol "⊘" placed over a conduit indicates that there is no fluid flow through the conduit in this configuration. Reference numerals indicating elements not mentioned in the discussion of FIG. 4 correspond to similar reference numerals in FIG. 1 beginning with a "1" rather than a "4" and are provided for ease of orientation of the reader.

In this configuration, working fluid 450 from the reservoir 402 is pumped by the steady flow pump 404 through the compliance chamber 406 and to the first 3-way control valve 422. The first 3-way control valve 422 is closed to the second 3-way control valve 424 and is open to the heat circulation conduit 352, thus shunting fluid flow back to the reservoir 302. As shown in FIG. 4, there is no fluid flow through the remaining elements of the test system. The second 3-way control valve 424 may be placed in any position as no fluid is passed from the first 3-way control valve 422. Both the variable 2-way control valve 440 and the 2-way control valve 444 may be placed in fully closed positions in this configuration to prevent working fluid from flowing out of the reservoir 402 into the rest of the test system 400.

Testing and test conditions may be controlled by a computer program executing on a computer connected to a control module that permits both input of test conditions and monitors feedback of the test conditions during a testing run. The software interface allows a user to control the test system flow, set critical test parameters, execute one or more tests automatically, and document the test results. The operator may input various system control and test parameters within the software interface, which may include, but are not limited to, transducer scaling parameters, measurement signal filtering parameters, fluid temperature set-point for heating, measurement allowance criteria for data acquisition, forward flow test flow rate target(s), back flow leakage test differential pressure target(s), and identification details for the test prosthesis.

The control software program on the computer may implement one more more test schedules to be run automatically by the controller on a valved prosthesis placed in the test conduit of the test system. The test schedules can automatically subject the valved prosthesis to a number of discrete steady flow hydrodynamic conditions (e.g., conditions mandated by standards organizations for testing) in succession without having to remove or adjust the valved prosthesis once mounted in the test system. In an example implementation, the computer executing the program may direct the fluid pump to pump the working fluid from the reservoir into the test system for each system configuration, i.e., forward and reverse flow.

In a forward flow configuration, the controller may configure a first valve in the test system (e.g., the second 3-way valve) to direct flow of the working fluid from the fluid pump through the test conduit holding the valved prosthesis. The valved prosthesis is thus positioned in-line with fluid flow in a forward flow direction from a proximal end of the test conduit to a distal end of the test conduit. Responsive to measurement values of a flow rate of the working fluid in the test system sensed by a flow rate sensor (e.g., the first flow meter) in the test system, the controller may adjust the pump rate of the fluid pump automatically to drive the fluid pump to achieve a stable target flow rate of the working fluid through the test system. The controller may automatically implement a first test schedule and adjust the pump rate of the fluid pump to change the flow rate to each of a plurality of prescribed flow rates according to the first test schedule. The pressure sensor may measure a pressure drop across the valved prosthesis for each prescribed flow rate in the first test schedule. The controller in communication with the pressure sensor receives each measured pressure drop for each prescribed flow rate in the first test schedule and passes the data to the computer program for recording.

In a reverse flow configuration, the controller may configure the first valve in the test system (e.g., the second 3-way valve) to direct flow of the working fluid from the fluid pump through the test conduit holding the valved prosthesis. In this configuration, the valved prosthesis is thus positioned in-line with fluid flow in a reverse flow direction from a distal end of the test conduit to a proximal end of the test conduit.

Responsive to measurement values of a differential pressure of the working fluid in the test system sensed by the pressure sensor, the controller may adjust the pump rate of the fluid pump to achieve a stable differential pressure of the working fluid across the valved prosthesis in the test conduit. The controller may automatically implement a second test schedule and adjust the pump rate of the fluid pump to change the differential pressure across the valved prosthesis to each of a plurality of prescribed differential pressures according to the second test schedule. The pressure sensor may measure a pressure differential across the valved prosthesis within the test conduit to confirm each prescribed differential pressure in the second test schedule is achieved while the working fluid flows in the reverse flow direction. The controller in communication with the flow meter (i.e., the second flow meter adjacent to the second 2-way valve) receives a leakage flow rate for each measured pressure differential for each prescribed differential pressure in the second test schedule receives each measured and passes the data to the computer program for recording.

Figure 5:
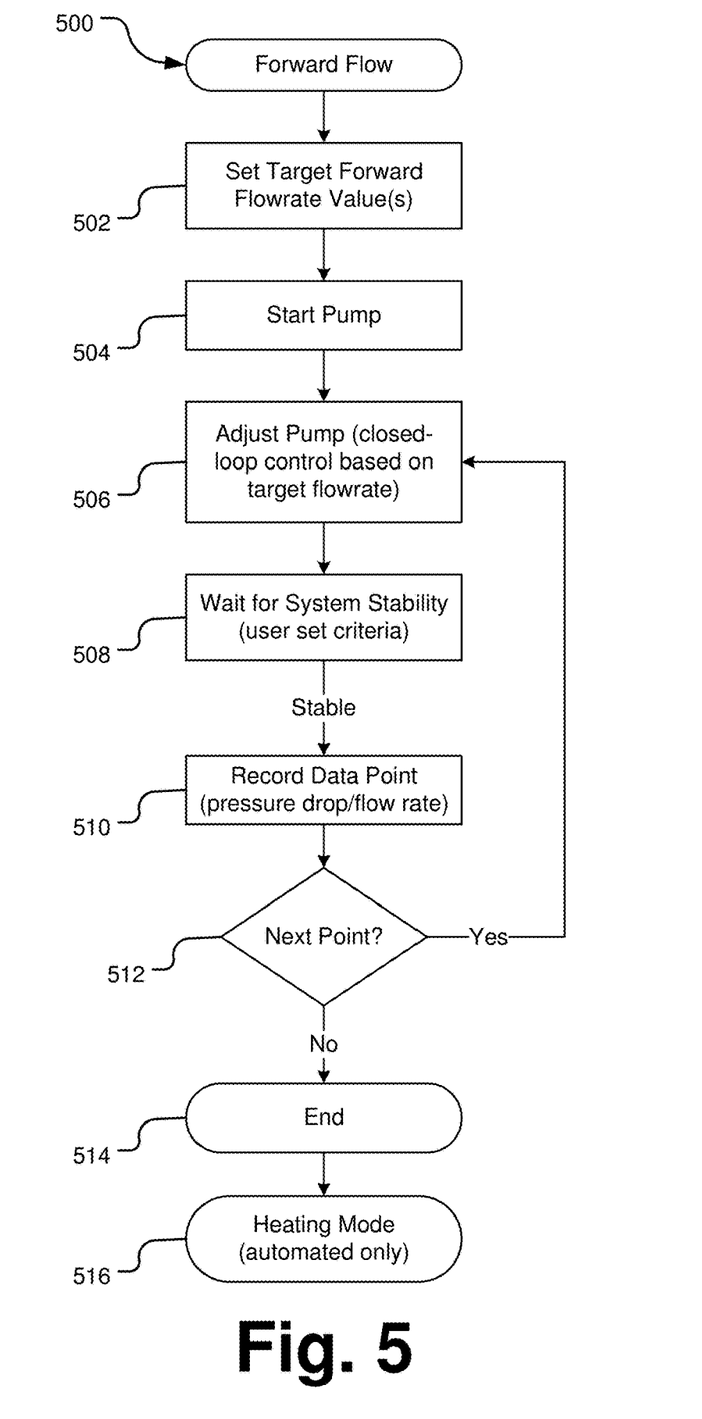
FIG. 5 is flow diagram of test system logic associated with operation of a forward flow test within the test system.

Process steps for performing a forward flow test 500 are depicted in the flow diagram of FIG. 5. When performing a forward flow pressure drop test, the primary test system control is the flowrate through the open test valve, values for which are initially set in operation 502. The system software will initiate the steady flow pump (operation 504) and adjust the computer controlled steady flow pump flowrate (operation 506) until the first test flowrate setpoint is achieved and stable within an operator defined tolerance (operation 508). After a stabilization period, the system control algorithm will acquire and store the relevant data from the system transducers (e.g., pressure drop, forward flowrate, fluid temperature, etc.) (operation 510). If additional test point data is required (decision 512), then the control system will adjust the steady flow pump flowrate to the next forward flowrate test point (return to operation 506). Again, after a stabilization period at the second test point (operation 508), the system control software will acquire and store the relevant data (operation 510) and then further adjust the steady flow pump flowrate to the next forward flowrate test point. This will continue until all the forward flowrate set points have been evaluated (decision 512), at which point the process will end (operation 514). In a test system under automatic control, the software program may be configured to place the test system in a circulation heating mode 516 in order to maintain the working fluid at a desired operating temperature until a new test cycle is initiated.

Figure 6:
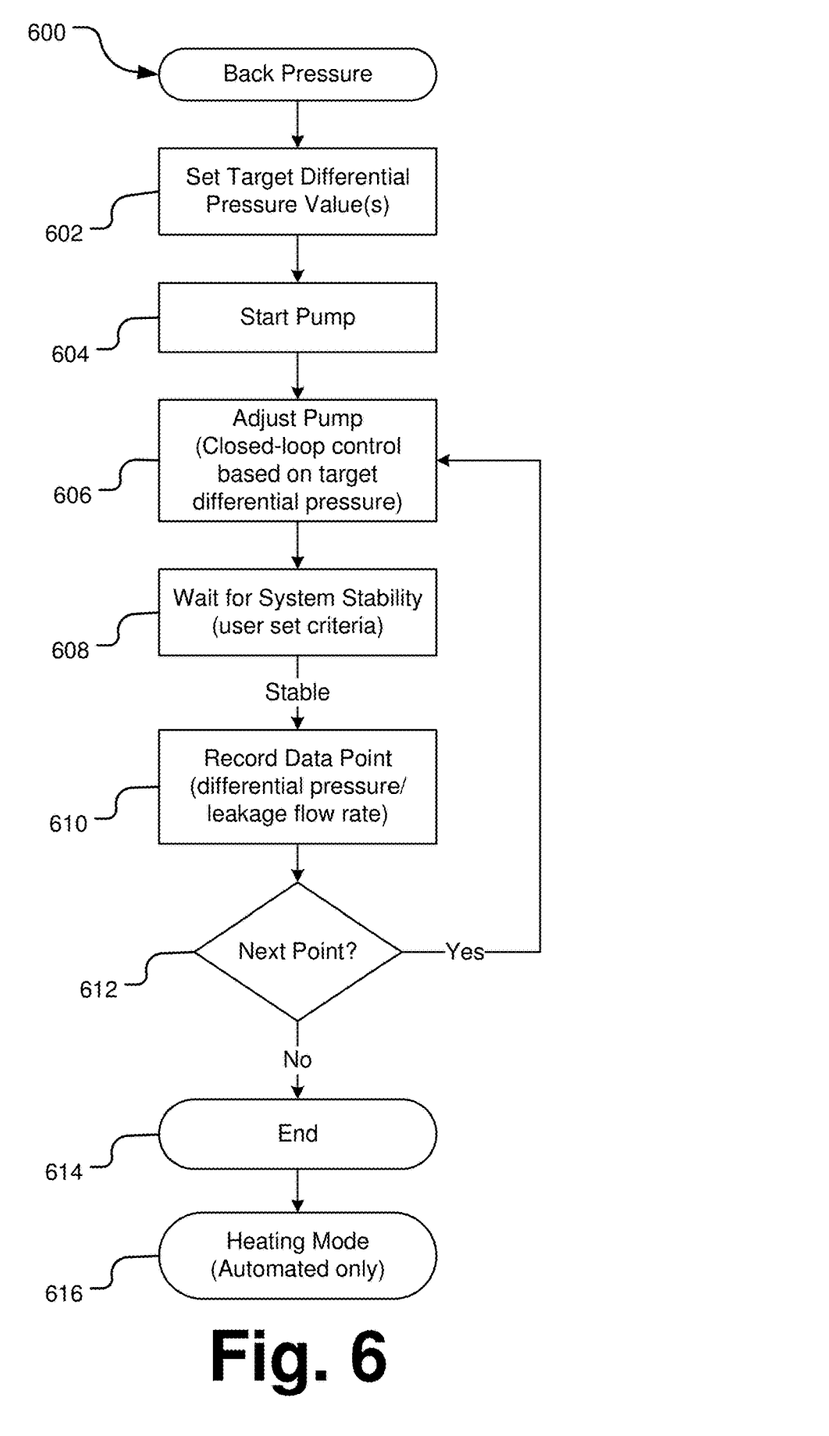
FIG. 6 is flow diagram of test system logic associated with operation of a back flow leakage test within the test system.

Process steps for performing a back pressure or back flow leakage test 600 are depicted in the flow diagram of FIG. 6. When performing a back flow leakage test, the primary test system control is the differential pressure across the closed test valve, values for which are initially set in operation 602. The system software will initiate the steady flow pump (operation 604) and adjust the computer controlled steady flow pump flowrate (operation 606) until the first differential pressure across the test valve point is achieved and stable within an operator defined tolerance (operation 608). After a stabilization period, the system control algorithm will acquire and store the relevant data from the system transducers (e.g., differential pressure across the valve, leakage flowrate, fluid temperature, etc.) (operation 610). If additional test point data is required (decision 512), then the control system will adjust the steady flow pump flowrate to load the valve at the next differential pressure test point (return to operation 606). Again, after a stabilization period at the second test point (operation 608), the system control software will acquire and store the relevant test data (operation 610) and then further adjust the steady flow pump flowrate to the next differential pressure test point. This will continue until all the backflow leakage pressure drop set points have been evaluated (decision 612), at which point the process will end (operation 614). In a test system under automatic control, the software program may be configured to place the test system in a circulation heating mode 616 in order to maintain the working fluid at a desired operating temperature until a new test cycle is initiated.

Figure 7:
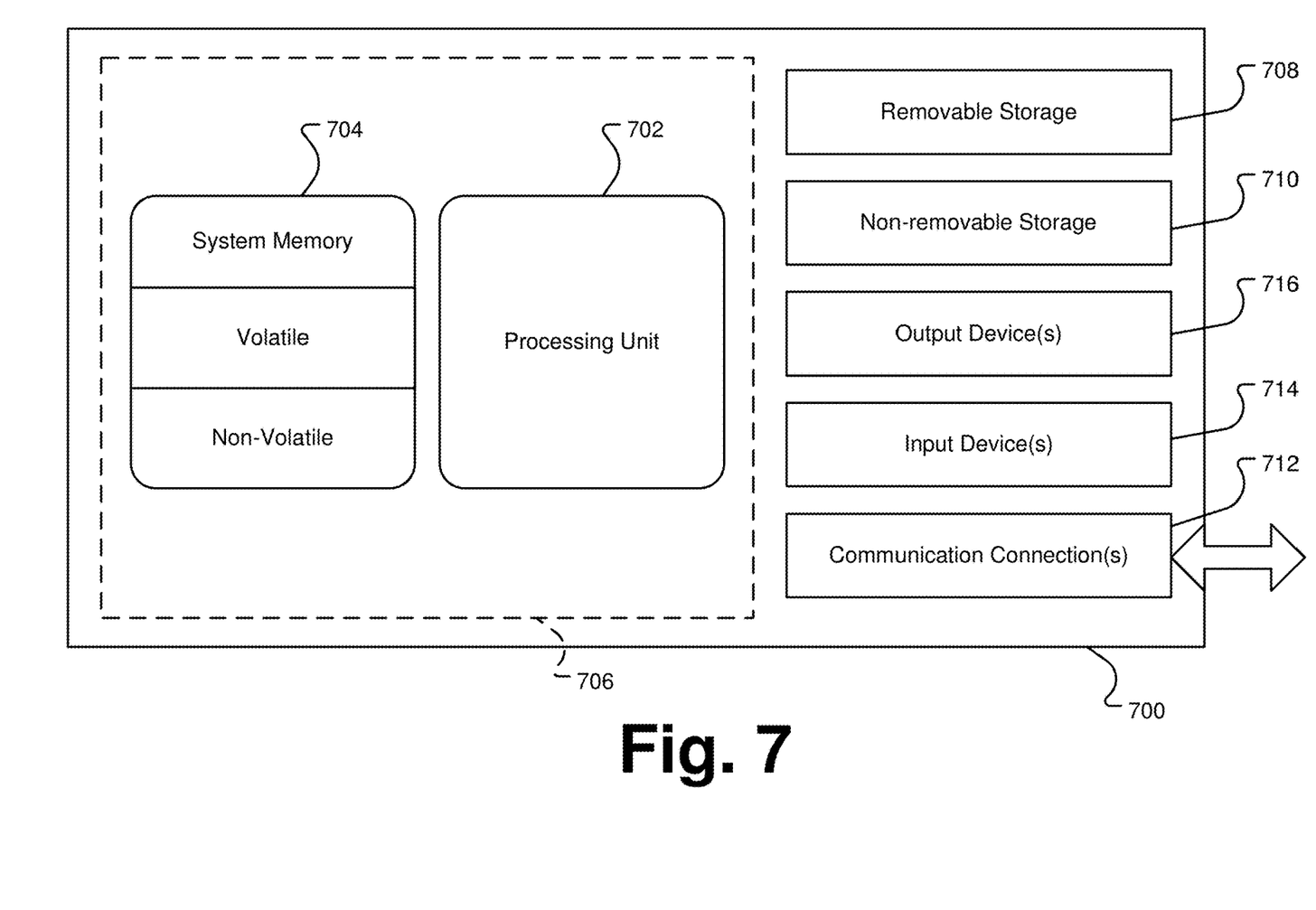
FIG. 7 is a schematic diagram of an exemplary computer system configured to operate a controller and data acquisition system to actuate and configure the test system.

FIG. 7 illustrates an exemplary computer system or other processing device 700 configured with control software to direct the control module of a test system for steady flow hydrodynamic performance measurement and testing as described herein. In one implementation, the processing device 700 typically includes at least one processing unit 702 and memory 704. Depending upon the exact configuration and type of the processing device 700, the memory 704 may be volatile (e.g., RAM), non-volatile (e.g., ROM and flash memory), or some combination of both. The most basic configuration of the processing device 700 need include only the processing unit 702 and the memory 704 as indicated by the dashed line 706.

The processing device 700 may further include additional devices for memory storage or retrieval. These devices may be removable storage devices 708 or non-removable storage devices 710, for example, memory cards, magnetic disk drives, magnetic tape drives, and optical drives for memory storage and retrieval on magnetic and optical media. Storage media may include volatile and nonvolatile media, both removable and non-removable, and may be provided in any of a number of configurations, for example, RAM, ROM, EEPROM, flash memory, CD-ROM, DVD, or other optical storage medium, magnetic cassettes, magnetic tape, magnetic disk, or other magnetic storage device, or any other memory technology or medium that can be used to store data and can be accessed by the processing unit 702. Additional instructions, e.g., in the form of software, interact with a base operating system to create a special purpose processing device 700. In this implementation, instructions for initiating the steady flow pump, adjusting the pump flowrate, monitoring, acquiring, and storing relevant data from system transducers (e.g., pressure drop, forward flowrate, differential pressure across the valve, leakage flowrate, fluid temperature, etc.) for closed loop control of the test system components may be stored in the memory 704 or on the storage devices 710 using any method or technology for storage of data, for example, computer readable instructions, data structures, and program modules. Data acquired from system transducers may also be stored in the memory 704 or on the storage devices 710.

The processing device 700 may also have one or more communication interfaces 712 that allow the processing device 700 to communicate with other devices, e.g., a control module and data acquisition system for sending control commands to and receiving sensor data from the test system. The communication interface 712 may be connected with a network. The network may be a local area network (LAN), a wide area network (WAN), a telephony network, a cable network, an optical network, the Internet, a direct wired connection, a wireless network, e.g., radio frequency, infrared, microwave, or acoustic, or other networks enabling the transfer of data between devices. Data is generally transmitted to and from the communication interface 712 over the network via a modulated data signal, e.g., a carrier wave or other transport medium. A modulated data signal is an electromagnetic signal with characteristics that can be set or changed in such a manner as to encode data within the signal.

The processing device 700 may further have a variety of input devices 714 and output devices 716. Exemplary input devices 714 may include a keyboard, a mouse, a tablet, and/or a touch screen device. Exemplary output devices 716 may include a video display, audio speakers, and/or a printer. Such input devices 714 and output devices 716 may be integrated with the processing device 700 or they may be connected to the processing device 700 via wires or wirelessly, e.g., via IEEE 802.11 or Bluetooth protocol. These integrated or peripheral input and output devices are generally well known and are not further discussed herein. Other functions, for example, handling network communication transactions, may be performed by the operating system in the nonvolatile memory 704 of the processing device 700.

The technology described herein may be implemented as logical operations and/or modules in one or more systems. The logical operations may be implemented as a sequence of processor-implemented steps executing in one or more computer systems and as interconnected machine or circuit modules within one or more computer systems. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the structures disclosed herein, and do not create limitations, particularly as to the position, orientation, or use of such structures. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A system for testing steady flow hydrodynamic performance of a valved prosthesis in both forward fluid flow and back fluid flow directions comprising
   a reservoir storing a working fluid;
   a fluid pump in fluid connection with the reservoir and configured to pump working fluid from the reservoir throughout the system;
   a test conduit with a proximal end and a distal end and configured to hold a valved prosthesis within a lumen of the test conduit;
   a pressure transducer configured to measure a pressure difference across the valved prosthesis held within the test conduit;
   a first conduit extending between and in fluid connection with the distal end of the test conduit and the reservoir;
   a variable first 2-way control valve positioned in line with the first conduit between the distal end of the test conduit and the reservoir;
   a second conduit extending between and in fluid connection with the proximal end of the test conduit and the reservoir;
   a first flow meter configured to measure a flow rate of the working fluid through the second conduit;
   a second 2-way control valve positioned in line with the second conduit between the proximal end of the test conduit and the reservoir; and
   a first 3-way control valve having an inlet in fluid connection with an outlet of the fluid pump, a first outlet in fluid connection with the proximal end of the test conduit, and a second outlet in fluid connection with the first conduit between the distal end of the test conduit and the variable first 2-way control valve, and configured to alternately direct the working fluid to either the test conduit or the first conduit exclusively;

wherein, without adjustment of the valved prosthesis within or removal of the valved prosthesis from the test conduit, in a first system configuration, the first 3-way control valve exclusively directs fluid flow to the proximal end of the test conduit and through the test conduit to the distal end, the variable first 2-way control valve is configured in a fully open position, the second 2-way control valve is configured in a fully closed position, and fluid flow is directed in a forward flow direction through the test conduit to pass through the valved prosthesis in an open position such that a first pressure drop value across the open valved prosthesis is measurable by the pressure transducer; and in a second system configuration, the first 3-way control valve exclusively directs fluid flow to the first conduit and through the test conduit from the distal end to the proximal end, the variable 2-way control valve is configured in a partially open position, the 2-way control valve is configured in a fully open position, and fluid flow is directed through the test conduit in a reverse flow direction to pass through the valved prosthesis in a closed position such that a fluid leakage flow rate through the closed valved prosthesis is measurable by the first flow meter.

2. The system of claim 1 further comprising a compliance chamber positioned between the fluid pump and the first 3-way control valve.

3. The system of claim 1, wherein the fluid pump is a steady flow pump.

4. The system of claim 1, wherein the reservoir is open to atmosphere.

5. The system of claim 1 further comprising a flow straightener positioned at the proximal end of the test conduit to reduce turbulent fluid flow from the first 3-way control valve through the test conduit.

6. The system of claim 1, wherein the test conduit is comprised of at least two conduit parts and the valved prosthesis is positioned between the at least two conduit parts.

7. The system of claim 1, wherein in the second system configuration, the variable first 2-way control valve is configured in a fully closed position.

8. The system of claim 1 further comprising
a second 3-way control valve positioned between the fluid pump and the first 3-way control valve and having an inlet in fluid connection with an outlet of the fluid pump, a first outlet in fluid connection with the inlet of the first 3-way control valve, and a second outlet; and
a heat circulation conduit in fluid connection at a first end with the second outlet of the second 3-way control valve and at a second end with the reservoir first conduit between the distal end of the test conduit and the variable first 2-way control valve; wherein
the second 3-way control valve is configured to alternately direct the working fluid to either the first 3-way control valve or the heat circulation conduit exclusively.

9. The system of claim 6 further comprising a compliance chamber positioned between the fluid pump and the second 3-way control valve.

10. The system of claim 1 further comprising a second flow meter positioned along the first conduit between the test conduit and the variable first 2-way valve.

11. The system of claim 1 further comprising
a controller in control communication with the fluid pump, the first 3-way control valve, the variable first 2-way control valve, and the second two way control valve, and in data communication with the pressure sensor and the first flow meter; and
a computer configured with a test implementation software program that directs functionality of the controller, wherein
when the controller is directed by the computer to automatically implement the first system configuration, a first test schedule is automatically implemented in the controller that adjusts the pump rate of the fluid pump to change the flow rate to each of a plurality of prescribed flow rates according to the test schedule, the pressure sensor measures a pressure drop across the valved prosthesis for each prescribed flow rate in the first test schedule, and the controller records each measured pressure drop for each prescribed flow rate in the first test schedule; and
when the controller is directed by the computer to automatically implement the second system configuration, a second test schedule is automatically implemented in the controller, that adjusts the pump rate of the fluid pump to change the pressure difference across the valved prosthesis to each of a plurality of prescribed differential pressures according to the second test schedule, the pressure transducer measures a pressure differential across the valved prosthesis for each prescribed differential pressure in the second test schedule, and the controller records the fluid leakage flow rate for each measured pressure differential for each prescribed differential pressure in the second test schedule.

12. A process implemented by a computer system for automatically controlling a test system for measuring steady flow hydrodynamic performance of a valved prosthesis in both forward fluid flow and reverse fluid flow directions without adjustment of the valved prosthesis within or removal of the valved prosthesis from the test conduit, the process comprising the following operations performed by the computer system:

directing the controller in control communication with a first valve downstream of the fluid pump to configure the first valve to direct flow of the working fluid from the fluid pump through a test conduit holding the valved prosthesis in-line with fluid flow in a forward flow direction from a proximal end of the test conduit to a distal end of the test conduit;

directing a controller in control communication with a fluid pump to instantiate pumping of a working fluid from a reservoir in the test system by the fluid pump;

receiving from the controller measurement values of a flow rate of the working fluid in the test system sensed by a flow rate sensor in the test system in data communication with the controller;

directing the controller to adjust a pump rate of the fluid pump to achieve a stable target flow rate of the working fluid through the test system based upon the flow rate measurement values received by the controller;

receiving from the controller measurement values of pressure drop through the valved prosthesis within the test conduit while the working fluid flows in the forward flow direction as sensed by a pressure sensor in the test system in data communication with the controller;

directing the controller to stop the fluid pump and reconfigure the first valve to direct flow of the working fluid through the test conduit and the valved prosthesis in a reverse flow direction from a distal end of the test conduit to a proximal end of the test conduit;

directing the controller to reinstantiate pumping of the working fluid from the reservoir by the fluid pump;

receiving from the controller measurement values of a pressure differential across the valved prosthesis within the test conduit as sensed by the pressure sensor;

directing the controller to adjust a pump rate of the fluid pump to achieve a stable target differential pressure of the working fluid across the valved prosthesis based upon the measurement values of the pressure differential; and receiving from the controller measurement values of leakage flow through the valved prosthesis sensed by a flow rate sensor in the test system in data communication with the controller while the working fluid flows in the reverse direction.

13. The process of claim 12 further comprising directing the controller to iteratively adjust the pump rate of the fluid pump to create different test system conditions while working fluid flows in both the forward flow direction and the reverse flow direction.

14. The process of claim 12, wherein the computer system further directs the controller in control communication with a second valve in the test system in fluid connection with the distal end of the test conduit and the reservoir to open the second valve while the first valve is configured to direct flow of the working fluid in the forward flow direction to allow working fluid to flow into the reservoir.

15. The process of claim 14, wherein the computer system further directs the controller in control communication with a third valve in the test system in fluid connection with the proximal end of the test conduit and the reservoir to open the third valve while the first valve is configured to direct flow of the working fluid in the reverse flow direction to allow working fluid to flow into the reservoir.

16. The process of claim 15, wherein the computer system further directs the controller to partially, but not entirely, close the second valve when the third valve is open and the first valve directs the working fluid in the reverse flow direction.

17. The process of claim 15, wherein the computer system further directs the controller to entirely close the third valve when the second valve is open and the first valve directs the working fluid in the forward flow direction.

18. The process of claim 15, wherein the computer system further directs the controller in control communication with a fourth valve in the test system in fluid connection with the fluid pump, the first valve, and the reservoir to configure the fourth valve to direct flow of the working fluid from the fluid pump to the reservoir.

19. The process of claim 12, wherein the test system is configured in the reverse flow direction before the test system is configured in the forward flow direction.

20. A method of operating a test system for measuring steady flow hydrodynamic performance of a valved prosthesis, the method comprising pumping a working fluid from a reservoir in the test system with a fluid pump;

in a forward flow configuration, configuring a first valve in the test system to direct flow of the working fluid from the fluid pump through a test conduit holding the valved prosthesis in-line with fluid flow in a forward flow direction from a proximal end of the test conduit to a distal end of the test conduit;

responsive to measurement values of a flow rate of the working fluid in the test system sensed by a flow rate sensor in the test system, adjusting a pump rate of the fluid pump automatically by a controller driving the fluid pump to achieve a stable target flow rate of the working fluid through the test system;

responsive to a first test schedule automatically implemented in the controller, adjusting the pump rate of the fluid pump to change the flow rate to each of a plurality of prescribed flow rates according to the first test schedule;

measuring with a pressure sensor in the test system a pressure drop across the valved prosthesis for each prescribed flow rate in the first test schedule; and recording, via the controller in communication with the pressure sensor, each measured pressure drop for each prescribed flow rate in the first test schedule; or in a reverse flow configuration, configuring the first valve in the test system to direct flow of the working fluid from the fluid pump through the test conduit holding the valved prosthesis in-line with fluid flow in a reverse flow direction from a distal end of the test conduit to a proximal end of the test conduit;

responsive to measurement values of a differential pressure of the working fluid in the test system sensed by the pressure sensor, adjusting the pump rate of the fluid pump to achieve a stable differential pressure of the working fluid across the valved prosthesis in the test conduit;

responsive to a second test schedule automatically implemented in the controller, adjusting the pump rate of the fluid pump to change the differential pressure across the valved prosthesis to each of a plurality of prescribed differential pressures according to the second test schedule;

measuring with the pressure sensor a pressure differential across the valved prosthesis within the test conduit for each prescribed differential pressure in the second test schedule while the working fluid flows in the reverse flow direction;

recording, via the controller in communication with a flow meter, a leakage flow rate for each measured pressure differential for each prescribed differential pressure in the second test schedule.

21. The method of claim 20, wherein operation of the test system is alternately configurable between measurement of the pressure drop in the forward flow direction and measurement of the leakage flow rate in the reverse flow direction without adjustment of the valved prosthesis within or removal of the valved prosthesis from the test conduit.

22. The method of claim 20 further comprising opening a second valve in the test system under control of the controller, wherein the second valve is in fluid connection with the distal end of the test conduit and the reservoir, to direct flow of the working fluid in the forward flow direction into the reservoir.

23. The method of claim 20 further comprising opening a third valve in the test system under control of the controller, wherein the third valve is in fluid connection with the proximal end of the test conduit and the reservoir, to direct flow of the working fluid in the reverse flow direction into the reservoir.

24. The method of claim 23 further comprising, under control of the controller, partially, but not entirely, closing the second valve when the third valve is open and the first valve directs the working fluid in the reverse flow direction.

25. The process of claim 23 further comprising, under control of the controller, entirely closing the third valve when the second valve is open and the first valve directs the working fluid in the forward flow direction.

26. The process of claim 23 further comprising configuring a fourth valve under control of the controller to direct flow of the working fluid from the fluid pump to the reservoir, wherein the fourth valve is in fluid connection with the fluid pump, the first valve, and the reservoir.

\* \* \* \* \*